US012759964B2

(12) United States Patent
Li et al.

(10) Patent No.: US 12,759,964 B2
(45) Date of Patent: Oct. 13, 2026

(54) METHOD FOR PREPARING PHENOXYCARBOXYLATE

(71) Applicant: SHANDONG WEIFANG RAINBOW CHEMICAL CO., LTD, Weifang (CN)

(72) Inventors: Zhiqing Li, Weifang (CN); Xiaopeng Huang, Weifang (CN); Cheng Wang, Weifang (CN); Fujun Han, Weifang (CN); Changtao Zhou, Weifang (CN); Qiang Liu, Weifang (CN); Qifan Wu, Weifang (CN); Guangli Zhao, Weifang (CN)

(73) Assignee: SHANDONG WEIFANG RAINBOW CHEMICAL CO., LTD, Weifang (CN)

( * ) Notice: Subject to any disclaimer, the term of this patent is extended or adjusted under 35 U.S.C. 154(b) by 474 days.

(21) Appl. No.: 18/401,394

(22) Filed: Dec. 30, 2023

(65) Prior Publication Data

US 2024/0217912 A1 Jul. 4, 2024

Related U.S. Application Data

(63) Continuation of application No. PCT/CN2023/132999, filed on Nov. 21, 2023.

(30) Foreign Application Priority Data

Dec. 30, 2022 (CN) ......................... 202211727068.0

(51) Int. Cl.
*C07C 67/08* (2006.01)

(52) U.S. Cl.
CPC .................................... *C07C 67/08* (2013.01)

(58) Field of Classification Search
CPC ....... C07C 67/08; C07C 37/66; C07C 39/235; C07C 39/44; C07C 67/31; C07C 69/708; C07C 69/712
See application file for complete search history.

(56) References Cited

PUBLICATIONS

CN 108503544 (A), Chen Guiyuan et al., Preparation method for 2,4-dichlorophenoxyacetic acid, machine translation, Sep. 7, 2018.*

* cited by examiner

*Primary Examiner* — Jafar F Parsa
(74) *Attorney, Agent, or Firm* — HAUPTMAN HAM, LLP

(57) ABSTRACT

A method for preparing a phenoxycarboxylate includes 1) allowing a salt of a phenolic compound and a halogenated carboxylate to subject to a condensation reaction in a polar solvent under the action of a catalyst; and 2) adding an acid-containing organic solvent to the condensation reaction liquid in step 1) to perform an acidification, and purifying the precipitated halogenated inorganic salt to obtain a phenoxycarboxylate. A catalyst is added in the condensation process, which can improve the reaction rate, achieve the reaction at room temperature and high material conversion rate, and avoid the problem in the prior art that the reaction needs to be performed at high temperature, about 120° C. After the condensation reaction is completed, the salt is removed by dry filtration (an anhydrous condition) by adding a methanol hydrogen chloride solution. There is no industrial wastewater, raw materials are easily recycled, and the reaction yield is high.

18 Claims, No Drawings

METHOD FOR PREPARING PHENOXYCARBOXYLATE

CROSS-REFERENCE

The present application is a Continuation of International Application Number PCT/CN2023/132999 filed Nov. 21, 2023, which claims priority to Chinese patent application No. 202211727068.0 filed at the China Patent Office on Dec. 30, 2022, and entitled "Method for preparing phenoxycarboxylate", the entire contents of which are incorporated by reference herein in their entireties.

TECHNICAL FIELD

The present application relates to the field of pesticides, in particular to a method for preparing a phenoxycarboxylate.

BACKGROUND ART

The synthesis route of a phenoxycarboxylate usually comprises: allowing a phenolic compound and an alkaline hydroxide or a carbonate to subject to dehydration into salt in an organic solvent to obtain a salt of the phenolic compound; and after salt formation, adding a chlorocarboxylate, performing a condensation reaction to obtain a mixed solution of a phenoxycarboxylate and a chlorate, performing water extraction, removing the chlorate by filtration, and performing crystallization to obtain a phenoxycarboxylate.

However, in the prior art, (1) the dehydration process of sodium phenolate is a heterogeneous reaction, wherein the temperature needs to be raised during dehydration, the energy consumption is high during dehydration, and the requirements for the equipment are relatively stringent as the solid-liquid two-phase equipment is easily blocked; (2) the condensation reaction requires high temperature, and has high energy consumption and high safety risk; (3) the dropwise addition of the chlorocarboxylate takes a lot of time, and a large amount of byproducts are generated; (4) the condensation reaction rate is low, and the reaction time is long, which seriously affects the reaction productivity; (5) the aftertreatment requires water extraction, and there are problems such as loss of products and raw materials, and generation of industrial wastewater; and (6) the conversion rate of the chloroacetate is low, and the recycle of phenol and methyl chloroacetate as raw materials is not considered.

SUMMARY OF THE INVENTION

Object of the Invention

In order to overcome the above-mentioned shortcomings, an object of the present application is to provide a method for preparing a phenoxycarboxylate. In the present application, a catalyst is added in the condensation process, which can improve the reaction rate, achieve the reaction at room temperature with low overall energy consumption and high material conversion rate, and avoid the problem in the prior art that the reaction needs to be performed at high temperature, about 120° C. After the condensation reaction is completed, the salt is removed by dry filtration (an anhydrous condition) by adding a methanol hydrogen chloride solution. There is no industrial wastewater, raw materials are easily recycled, the reaction yield is high, and the following problems are solved: water extraction, crystallization, etc.

need to be performed in the prior art to obtain the product and industrial wastewater and high energy consumption are caused thereby.

Solutions

In order to achieve the object of the present application, the technical solutions used by the present application are as follows.

In a first aspect, the present application provides a method for preparing a phenoxycarboxylate, comprising:

1) allowing a salt of a phenolic compound and a halogenated carboxylate to subject to a condensation reaction in a polar solvent under the action of a catalyst; and
2) adding an acid-containing organic solvent to the condensation reaction liquid in step 1) to perform an acidification, and purifying the precipitated halogenated inorganic salt to obtain a phenoxycarboxylate.

In the present application, the addition of a catalyst in the condensation process can improve the reaction rate, and achieve the reaction at room temperature with low overall energy consumption and high material conversion rate. In the present application, performing an acidification in an acid-containing organic solvent avoids the addition of water, removing the salt by means of dry filtration avoids the generation of industrial wastewater, raw materials are simple to recycle, and the reaction yield is high.

Further, in step 1), the catalyst comprises a pyridine catalyst, which is one or more selected from the group consisting of 4-dimethylaminopyridine and 4-pyrrolidinylpyridine; and optionally, the mass ratio of the catalyst to the halogenated carboxylate is 0.02-1:100, optionally 0.05–0.2:100, optionally 0.07–0.15:100, and optionally 0.073–0.14:100.

Further, in step 1), the halogenated carboxylate is chlorocarboxylate, and optionally comprises one or more of methyl chloroacetate, ethyl chloroacetate and isooctyl chloroacetate; optionally, the precipitated halogenated inorganic salt in step 2) is a chlorinated inorganic salt; and optionally, the precipitated halogenated inorganic salt in step 2) is sodium chloride.

Further, in step 1), the salt of a phenolic compound comprises one or more of phenolate, o-cresolate, 2,4-dichlorophenolate, and 4-chloro-2-methylphenolate; and optionally, the salt of a phenolic compound comprises one or more of sodium phenolate, sodium o-cresolate, sodium 2,4-dichlorophenolate, and sodium 4-chloro-2-methylphenolate.

Further, in step 1), the polar solvent comprises one or more of N,N-dimethylacetamide, N,N-dimethylaminoformamide and methyl isobutyl ketone, and is optionally methyl isobutyl ketone.

Further, in step 1), the molar ratio of the salt of a phenolic compound to the halogenated carboxylate is 1:0.96-1.02, optionally 1:0.098-1.01, and optionally 1:1; Further, in step 1), the mass ratio of the salt of a phenolic compound to the polar solvent is 1: 1-20, and optionally 1: 2-18.

Further, in step 1), the temperature of the condensation reaction is −20° C. to 80° C., optionally 15-60° C., optionally 15-40° C., and optionally 20-30° C.

Further, in step 1), the time of the condensation reaction is 0.05-2 h, optionally 0.1-2 h, optionally 0.1–0.5 h, optionally 0.1–0.3 h, and optionally 0.1–0.2 h.

Further, in step 1), the halogenated carboxylate is added dropwise, and optionally, the time of dropwise addition is 0-3 h, and optionally 0–0.5 h.

Further, in step 2), the acid-containing organic solvent has no water or has low water content.

Further, in step 2), the acid-containing organic solvent comprises one or two of a methanol hydrogen chloride solution and an ethanol hydrogen chloride solution, and is optionally a methanol hydrogen chloride solution.

Further, in step 2), the method for purifying the precipitated halogenated inorganic salt to obtain a phenoxycarboxylate comprises: recycling the solvent and unreacted raw materials by means of distillation to obtain a phenoxycarboxylate; and optionally, the distillation method is negative-pressure distillation.

Further, in step 1), the method for preparing the salt of a phenolic compound comprises: allowing a phenolic compound and a metal hydroxide to subject to dehydration into salt in a polar solvent to obtain the salt of a phenolic compound; and optionally, the polar solvent is used as the polar solvent in step 1).

In the present application, the polar solvent used in the salt formation process solves the problem that a large amount of salt precipitate out in the dehydration process, avoids the risk of explosion, and solves the disadvantage of separation when the mixed solvent is recycled, so that the system always maintains a uniform state in the entire dehydration and condensation process. Moreover, negative-pressure dehydration is used in the dehydration process, which reduces the dehydration temperature and rate, achieves continuous production, greatly improves the dehydration efficiency, and greatly reduces energy consumption.

Further, the phenolic compound comprises one or more of phenol, o-cresol, 2,4-dichlorophenol and 4-chloro-2-methylphenol.

Further, the metal hydroxide comprises one or more of sodium hydroxide, potassium hydroxide, calcium hydroxide, magnesium hydroxide and aluminum hydroxide; optionally, the metal hydroxide comprises one or more of sodium hydroxide, potassium hydroxide and calcium hydroxide; optionally, the metal hydroxide is added in a form of an aqueous solution or a solid; and optionally, the mass fraction of the metal hydroxide is 30% or more.

Further, the condition for dehydration into salt is that dehydration into salt is performed with negative-pressure distillation; optionally, the intensity of pressure of negative-pressure distillation is −0.09 MPa to −0.098 MPa.

Further, the mass ratio of the phenolic compound to the polar solvent is 1: 1-20, and optionally 1:2-18 in dehydration into salt.

Further, the temperature of dehydration into salt is 50-120° C., and optionally 50-90° C.

Further, the time of dehydration into salt is 1-2 h.

Further, the molar ratio of the phenolic compound to the metal hydroxide is 1:0.97-1, optionally 1:0.97–0.99, and optionally 1:0.98 in dehydration into salt.

Beneficial Effects (1) In the present application, the addition of a catalyst in the condensation process can improve the reaction rate, and achieve the reaction at room temperature with low overall energy consumption and high material conversion rate. In the present application, performing an acidification in an acid-containing organic solvent avoids the addition of water, removing the salt by means of dry filtration avoids the generation of industrial wastewater, raw materials are simple to recycle, and the reaction yield is high.

(2) In the present application, the polar solvent used in the salt formation process solves the problem that a large amount of salt precipitate out in the dehydration process, avoids the risk of explosion, and solves the disadvantage of separation when the mixed solvent is recycled, so that the system always maintains a uniform state in the entire dehydration and condensation process. Moreover, negative-pressure dehydration is used in the dehydration process, which reduces the dehydration temperature and rate, achieves continuous production, greatly improves the dehydration efficiency, and greatly reduces energy consumption.

DETAILED DESCRIPTION OF THE INVENTION

In order to make the purpose, technical solutions and advantages of the present application clearer, the technical solutions in the examples of the present application will be described clearly and completely. Obviously, the described examples are some of the examples of the present application, but not all of them. Based on the examples of the present invention, all other examples obtained by those of ordinary skill in the art without creative work are falling within the protection scope of the present invention.

In addition, in order to better explain the present application, a lot of specific details are given in the following examples. It will be understood by those skilled in the art that the present application may be implemented without certain specific details. In some examples, materials, solutions, methods, means, etc., well known to those skilled in the art, are not described in detail so as to highlight the spirit of the present application.

Throughout the specification and claims, the term "comprising" or variations thereof, such as "including" or "containing", will be understood to include the stated components and not to exclude other elements or other components, unless expressly indicated otherwise.

The product content in the following examples is confirmed by liquid-phase or gas-phase chromatographic instruments. In the reaction process, the purity and yield are calculated using an external standard method.

Raw materials such as phenol, sodium hydroxide, methyl isobutyl ketone and 4-dimethylaminopyridine (DMAP) in the following examples are commercially available.

Example 1 Preparation of Methyl Phenoxyacetate

Firstly, the system was replaced by nitrogen. 100 g of phenol and 83.3 g of 50% sodium hydroxide aqueous solution were uniformly mixed in a molar ratio of 1:0.98. 400 g of methyl isobutyl ketone as a solvent was added to make sodium phenolate form a homogeneous solution, and dehydration by negative-pressure distillation was performed (under a negative-pressure condition of −0.096 MPa). After the dehydrated state was qualified, 0.11 g of 4-dimethylaminopyridine (DMAP) as a catalyst was added, 113 g of methyl chloroacetate was dropwise added at room temperature for 0.1 h to perform a condensation reaction, and heat preservation was performed for 0.1 h during the reaction. After heat preservation was completed, a methanol hydrogen chloride solution was added to perform an acidification, and sodium chloride was separated by means of filtration. 398 g of methyl isobutyl ketone as a solvent and 1.9 g of unreacted raw material phenol were recycled by means of negative-pressure distillation for reuse, and finally 172.5 g of a product, i.e., methyl phenoxyacetate, was obtained, with a content of 99% and a yield of 99%.

Example 2 Preparation of Methyl o-Methylphenoxyacetate 100 g of o-cresol and 72.5 g of 50% sodium hydroxide aqueous solution were uniformly mixed in a molar ratio of 1:0.98. 400 g of methyl isobutyl ketone as a solvent was added to make sodium phenolate form a homogeneous solution, and dehydration by negative-pressure distillation was performed (under a negative-pressure condition of −0.096 MPa). After the dehydrated state was qualified, 0.098 g of 4-dimethylaminopyridine (DMAP) as a catalyst was added, 98.36 g of methyl chloroacetate was dropwise added at room temperature for 0.1 h to perform a condensation reaction, and heat preservation was performed for 0.1 h during the reaction. After heat preservation was completed, a methanol hydrogen chloride solution was added to perform an acidification, and sodium chloride was separated by means of filtration. 397.5 g of methyl isobutyl ketone as a solvent and 2.1 g of unreacted raw material o-cresol were recycled by means of negative-pressure distillation for reuse, and finally 161.8 g of a product, i.e., methyl o-methylphenoxyacetate, was obtained, with a content of 99.0% and a yield ≥99%.

Example 3 Preparation of Methyl 2,4-Dichlorophenoxyacetate

Firstly, the system was replaced by nitrogen. 100 g of 2,4-dichlorophenol and 48.1 g of 50% sodium hydroxide aqueous solution were uniformly mixed in a molar ratio of 1:0.98. 400 g of methyl isobutyl ketone as a solvent was added to make sodium phenolate form a homogeneous solution, and dehydration by negative-pressure distillation was performed (under a negative-pressure condition of −0.096 MPa). After the dehydrated state was qualified, 0.096 g of 4-dimethylaminopyridine (DMAP) as a catalyst was added, 65.2 g of methyl chloroacetate was dropwise added at room temperature for 0.1 h to perform a condensation reaction, and heat preservation was performed for 0.1 h during the reaction. After heat preservation was completed, a methanol hydrogen chloride solution was added to perform an acidification, and sodium chloride was separated by means of filtration. 396.5 g of methyl isobutyl ketone as a solvent and 3.2 g of unreacted raw material 2,4-dichlorophenol were recycled by means of negative-pressure distillation for reuse, and finally 141.3 g of a product, i.e., methyl 2,4-dichlorophenoxyacetate, was obtained, with a content of 99.0% and a yield ≥99%.

Example 4 Preparation of Methyl 4-Chloro-2-Methylphenoxyacetate

Firstly, the system was replaced by nitrogen. 100 g of 4-chloro-2-methylphenol and 55 g of 50% sodium hydroxide aqueous solution were uniformly mixed in a molar ratio of 1:0.98. 403 g of methyl isobutyl ketone as a solvent was added to make sodium phenolate form a homogeneous solution, and dehydration by negative pressure distillation was performed (under a negative-pressure condition of −0.096 MPa). After the dehydrated state was qualified, 0.074 g of 4-dimethylaminopyridine (DMAP) as a catalyst was added, 74.6 g of methyl chloroacetate was dropwise added at room temperature for 0.1 h to perform a condensation reaction, and heat preservation was performed for 0.1 h during the reaction. After heat preservation was completed, a methanol hydrogen chloride solution was added to perform an acidification, and sodium chloride was separated by means of filtration. 398 g of methyl isobutyl ketone as a solvent and 2.85 g of unreacted raw material 4-chloro-2-methylphenol were recycled by means of negative-pressure distillation for reuse, and finally 144.8 g of a product, i.e., methyl 4-chloro-2-methylphenoxyacetate, was obtained, with a content of 99.5% and a yield of 99%.

Example 5 Preparation of Ethyl Phenoxyacetate

Firstly, the system was replaced by nitrogen. 100 g of phenol and 83.32 g of 50% sodium hydroxide aqueous solution were uniformly mixed in a molar ratio of 1:0.98. 400 g of methyl isobutyl ketone as a solvent was added to make sodium phenolate form a homogeneous solution, and dehydration by negative-pressure distillation was performed (under a negative-pressure condition of −0.096 MPa). After the dehydrated state was qualified, 0.12 g of 4-dimethylaminopyridine (DMAP) as a catalyst was added, 127.5 g of ethyl chloroacetate was dropwise added at room temperature for 0.1 h to perform a condensation reaction, and heat preservation was performed for 0.1 h during the reaction. After heat preservation was completed, a methanol hydrogen chloride solution was added to perform an acidification, and sodium chloride was separated by means of filtration. 398 g of methyl isobutyl ketone as a solvent and 1.78 g of unreacted raw material phenol were recycled by means of negative-pressure distillation for reuse, and finally 187.6 g of a product, i.e., ethyl phenoxyacetate, was obtained, with a content of 99.5% and a yield ≥99%.

Example 6 Preparation of Ethyl o-Methylphenoxyacetate

Firstly, the system was replaced by nitrogen. 100 g of o-cresol and 71.9 g of 50% sodium hydroxide aqueous solution were uniformly mixed in a molar ratio of 1:0.97. 401 g of methyl isobutyl ketone as a solvent was added to make sodium phenolate form a homogeneous solution, and dehydration by negative-pressure distillation was performed (under a negative-pressure condition of −0.096 MPa). After the dehydrated state was qualified, 0.11 g of 4-dimethylaminopyridine (DMAP) as a catalyst was added, 111 g of ethyl chloroacetate was dropwise added at room temperature for 0.1 h to perform a condensation reaction, and heat preservation was performed for 0.1 h during the reaction. After heat preservation was completed, a methanol hydrogen chloride solution was added to perform an acidification, and sodium chloride was separated by means of filtration. 399.5 g of methyl isobutyl ketone as a solvent and 2.2 g of unreacted raw material o-cresol were recycled by means of negative-pressure distillation for reuse, and finally 173.5 g of a product, i.e., ethyl o-methylphenoxyacetate, was obtained, with a content of 99.5% and a yield ≥99%.

Example 7 Preparation of Ethyl 2,4-Dichlorophenoxyacetate

Firstly, the system was replaced by nitrogen. 100 g of 2,4-dichlorophenol and 48.1 g of 50% sodium hydroxide aqueous solution were uniformly mixed in a molar ratio of 1:0.98. 400 g of methyl isobutyl ketone as a solvent was added to make sodium phenolate form a homogeneous solution, and dehydration by negative-pressure distillation was performed (under a negative-pressure condition of −0.096 MPa). After the dehydrated state was qualified, 0.073 g of 4-dimethylaminopyridine (DMAP) as a catalyst was added, 73.65 g of ethyl chloroacetate was dropwise added at room temperature for 0.1 h to perform a condensation reaction, and heat preservation was performed for 0.1 h during the reaction. After heat preservation was completed, a methanol hydrogen chloride solution was added to perform an acidification, and sodium chloride was separated by means of filtration. 396.5 g of methyl isobutyl ketone as a solvent and 3.16 g of unreacted raw material 2,4-dichlorophenol were recycled by means of negative-pressure distillation for reuse, and finally 149.7 g of a product, i.e., ethyl 2,4-dichlorophenoxyacetate, was obtained, with a content of 99.5% and a yield ≥99%.

Example 8 Preparation of Ethyl 4-Chloro-2-Methylphenoxyacetate

Firstly, the system was replaced by nitrogen. 100 g of 4-chloro-2-methylphenol and 55 g of 50% sodium hydroxide aqueous solution were uniformly mixed in a molar ratio of 1:0.98. 403 g of methyl isobutyl ketone as a solvent was added to make sodium phenolate form a homogeneous solution, and dehydration by negative-pressure distillation was performed (under a negative-pressure condition of −0.096 MPa). After the dehydrated state was qualified, 0.084 g of 4-dimethylaminopyridine (DMAP) as a catalyst was added, 84.2 g of ethyl chloroacetate was dropwise added at room temperature for 0.1 h to perform a condensation reaction was performed, and heat preservation was performed for 0.1 h during the reaction. After heat preservation was completed, a methanol hydrogen chloride solution was added to perform an acidification, and sodium chloride was separated by means of filtration. 398 g of methyl isobutyl ketone as a solvent and 2.85 g of unreacted raw material 4-chloro-2-methylphenol were recycled by means of negative-pressure distillation for reuse, and finally 154.5 g of a product, i.e., ethyl 4-chloro-2-methylphenoxyacetate, was obtained, with a content of 99.5% and a yield of 99%.

Example 9 Preparation of Isooctyl 2,4-Dichlorophenoxyacetate

Firstly, the system was replaced by nitrogen. 100 g of 2,4-dichlorophenol and 48.1 g of 50% sodium hydroxide aqueous solution were uniformly mixed in a molar ratio of 1:0.98. 403 g of methyl isobutyl ketone as a solvent was added to make sodium phenolate form a homogeneous solution, and dehydration by negative-pressure distillation was performed (under a negative-pressure condition of −0.096 MPa). After the dehydrated state was qualified, 0.12 g of 4-dimethylaminopyridine (DMAP) as a catalyst was added, 124.2 g of isooctyl chloroacetate was dropwise added at room temperature for 0.1 h to perform a condensation reaction, and heat preservation was performed for 0.1 h during the reaction. After heat preservation was completed, a methanol hydrogen chloride solution was added to perform an acidification, and sodium chloride was separated by means of filtration. 396.5 g of methyl isobutyl ketone as a solvent and 3.3 g of unreacted raw material 2,4-dichlorophenol were recycled by means of negative-pressure distillation for reuse, and finally 200.4 g of a product, i.e., isooctyl 2,4-dichlorophenoxyacetate, was obtained, with a content of 99.5% and a yield ≥99%.

Example 10 Preparation of Isooctyl 4-Chloro-2-Methylphenoxyacetate

Firstly, the system was replaced by nitrogen. 100 g of 4-chloro-2-methylphenol and 55 g of 50% sodium hydroxide aqueous solution were uniformly mixed in a molar ratio of 1:0.98. 403 g of methyl isobutyl ketone as a solvent was added to make sodium phenolate form a homogeneous solution, and dehydration by negative-pressure distillation were performed (under a negative-pressure condition of −0.096 MPa). After the dehydrated state was qualified, 0.14 g of 4-dimethylaminopyridine (DMAP) as a catalyst was added, 142 g of isooctyl chloroacetate was dropwise added at room temperature for 0.1 h to perform a condensation reaction, and heat preservation was performed for 0.1 h during the reaction. After heat preservation was completed, a methanol hydrogen chloride solution was added to perform an acidification, and sodium chloride was separated by means of filtration. 398 g of methyl isobutyl ketone as a solvent and 2.85 g of unreacted raw material 4-chloro-2-methylphenol were recycled by means of negative-pressure distillation for reuse, and finally 214.7 g of a product, i.e., isooctyl 4-chloro-2-methylphenoxyacetate, was obtained, with a content of 99.5% and a yield of 99%.

Comparative Example 1

47.6 g (0.5 mol) of phenol, 120 g of xylene, 30 g of butanol, and 62.8 g (0.5 mol) of sodium hydroxide aqueous solution with a mass fraction of 32% were mixed and stirred, the temperature was raised to about 140° C., and the reaction was performed in the presence of water for 1 h. The neutralization liquid was slightly cooled to 120° C., 53.8 g (0.495 mol) of methyl chloroacetate was dropwise added for 4 h, the temperature was raised to 146° C., and the reaction was performed for 2 h while heat preservation was performed. The reaction liquid was cooled to 100° C., 150 g of water was added, the pH was adjusted to 7, and the resulting solution was allowed to stand for layering. 20 g of xylene was added to the aqueous layer, and extraction was performed. The organic layer was separated by vacuum distillation to obtain 81.75 g of a product with a purity of 99.1% and a yield of 98%. Although the product in this comparative example had high purity and yield, the temperature needed to be raised during dehydration, and the purification needed to be conducted by extraction, increasing the cost of separation.

Comparative Example 2

Firstly, the system was replaced by nitrogen. 100 g of phenol and 130.1 g of 32% sodium hydroxide aqueous solution were uniformly mixed in a molar ratio of 1:0.98. 400 g of methyl isobutyl ketone as a solvent was added to make sodium phenolate form a homogeneous solution, and dehydration by negative-pressure distillation was performed (under a negative-pressure condition of −0.096 MPa). After the dehydrated state was qualified, no catalyst was added, 110.7 g of methyl chloroacetate was dropwise added at room temperature for 0.5 h to perform a condensation reaction, and heat preservation was performed for 0.5 h in the reaction. After heat preservation was completed, a methanol hydrogen chloride solution was added to perform an acidification, and sodium chloride was separated by means of filtration. 398 g of methyl isobutyl ketone as a solvent and 90 g of raw material phenol were recycled by means of negative-pressure distillation for reuse, 99.63 g of methyl chloroacetate was recycled for reuse, and finally 16.87 g of a product, i.e., methyl phenoxyacetate, was obtained with a content of 99% and a yield of 10%. The result analysis showed that the conversion rates of methyl chloroacetate and phenol were only 10%.

The present application uses a polar solvent to make the salt of a phenolic compound form a homogeneous solution, and uses dehydration by negative-pressure distillation to improve the dehydration rate. A catalyst is added to the homogeneous sodium phenolate solution obtained after the dehydrated state is qualified to perform a condensation reaction, which can improve the condensation reaction rate, the conversion rate of chloroacetate (99.99%) and the yield (99.5% or more), and can reduce the condensation reaction temperature (the reaction can be achieved at room temperature), i.e., reduce the overall energy consumption (the energy consumption is reduced by about 50%, and the polar solvent used is not azeotropic with water, which reduces the loss of heat due to azeotropy). In this reaction process, sodium chloride particles generated can be increased by using a low reaction temperature, the separation of the salt can be achieved simply by means of suction filtration, and the separation can be achieved using conventional equipment, which reduces the difficulty of aftertreatment. An acid-containing organic solvent solution is added and acidification is performed, and therefore phenolic compounds and methyl chloroacetate can be recycled without adding water for washing. The absence of water in the reaction avoids the hydrolysis of the product and the loss of raw materials in wastewater, improves the yield of raw materials and reduces the amount of hazardous waste generated, the yield of the separated condensed liquid can reach 99.5%, and the obtained product has a purity not less than 99.5% and can be directly used in subsequent reactions.

In the present application, dehydration into salt of phenolic compounds is performed in a polar solvent, and the system always maintains a uniform state in the dehydration process. Therefore, continuous production is achieved, and the dehydration efficiency is high, and the efficiency of the entire production process is high. Moreover, the raw materials are easy to obtain, the production cycle is short, the energy consumption is low, and the production cost is low. The generated chlorate is removed by means of filtration, and zero generation and zero discharge of wastewater are achieved.

In the present application, the use of a polar solvent such as methyl isobutyl ketone can make sodium phenolate form a homogeneous solution in the process of producing sodium phenolate, the dehydration rate is high, and the solution is still a homogeneous solution in the condensation process, which can improve the condensation reaction rate. In the present application, a catalyst DMAP is added in the condensation process, which can improve the reaction rate, achieve the reaction at room temperature with low overall energy consumption and high material conversion rate, and avoids the problem in the prior art that the reaction needs to be performed at high temperature, about 120° C. After the condensation reaction is completed, the salt is removed by dry filtration (an anhydrous condition) by adding a methanol hydrogen chloride solution. There is no industrial wastewater, raw materials are easily recycled, the reaction yield is high, and the following problems are solved: water extraction, crystallization, etc. need to be performed in the prior art to obtain the product and industrial wastewater and high energy consumption are caused thereby.

Finally, it should be noted that: the above-mentioned examples are only used to illustrate the technical solution of the present application, rather than to limit them. Although the present application is described in detail with reference to the foregoing examples, a person skilled in the art should understand that it is still possible to amend the technical solutions described in the foregoing examples or to make equivalent replacements to some of the technical features thereof; and these amendments or replacements should not make the essence of the corresponding technical solutions deviate from the spirit and scope of the technical solutions of the examples of the present application.

INDUSTRIAL APPLICABILITY

The present application discloses a method for preparing a phenoxycarboxylate, comprising: 1) allowing a salt of a phenolic compound and a halogenated carboxylate to subject to a condensation reaction in a polar solvent under the action of a catalyst; and 2) adding an acid-containing organic solvent to the condensation reaction liquid in step 1) to perform an acidification, and purifying the precipitated halogenated inorganic salt to obtain a phenoxycarboxylate. The present application adds a catalyst in the condensation process, which can accelerate the reaction rate and achieve the reaction at room temperature, with low overall energy consumption and high material conversion rate, avoiding the problem of high temperature reaction that needs to be carried out at about 120° C. in the prior art.

The invention claimed is:

1. A method for preparing a phenoxycarboxylate, wherein the method comprises:

1) allowing a salt of a phenolic compound and a halogenated carboxylate to subject to a condensation reaction in a polar solvent under the action of a catalyst; and
2) adding an acid-containing organic solvent to the condensation reaction liquid in step 1) to perform an acidification, and purifying the precipitated halogenated inorganic salt to obtain a phenoxycarboxylate.

2. The preparation method according to claim 1, wherein in step 1), the catalyst comprises a pyridine catalyst; optionally, the pyridine catalyst is one or more selected from the group consisting of 4-dimethylaminopyridine and 4-pyrrolidinylpyridine; optionally, the mass ratio of the catalyst to the halogenated carboxylate is 0.02-1:100, or 0.05-0.2:100, or 0.07-0.15:100, or 0.073-0.14:100, and optionally 0.073-0.14:100;

and/or, in step 1), the halogenated carboxylate is chlorocarboxylate, and optionally comprises one or more of methyl chloroacetate, ethyl chloroacetate and isooctyl chloroacetate; optionally, the precipitated halogenated inorganic salt in step 2) is a chlorinated inorganic salt; optionally, the precipitated halogenated inorganic salt in step 2) is sodium chloride;

and/or, in step 1), the salt of a phenolic compound comprises one or more of phenolate, o-cresolate, 2,4-dichlorophenolate, and 4-chloro-2-methylphenolate; optionally, the salt of a phenolic compound comprises one or more of sodium phenolate, sodium o-cresolate, sodium 2,4-dichlorophenolate, and sodium 4-chloro-2-methylphenolate;

and/or, in step 1), the polar solvent comprises one or more of N,N-dimethylacetamide, N,N-dimethylaminoformamide and methyl isobutyl ketone, and is optionally methyl isobutyl ketone.

3. The preparation method according to claim 1, wherein in step 1), the molar ratio of the salt of a phenolic compound to the halogenated carboxylate is 1:0.96-1.02, or 1:0.098-1.01, or 1:1, and optionally 1:1;

and/or, in step 1), the mass ratio of the salt of a phenolic compound to the polar solvent is 1:1-20, or 1:2-18.

4. The preparation method according to claim 2, wherein in step 1), the molar ratio of the salt of a phenolic compound to the halogenated carboxylate is 1:0.96-1.02, or 1:0.098-1.01, or 1:1, and optionally 1:1;

and/or, in step 1), the mass ratio of the salt of a phenolic compound to the polar solvent is 1:1-20, or 1:2-18.

5. The preparation method according to claim 1, wherein in step 1), the temperature of the condensation reaction is -20 °C to 80 °C or 15-60 °C or 15-40 °C or 20-30 °C;

and/or, in step 1), the time of the condensation reaction is 0.05-2 h, or 0.1-2 h, or 0.1-0.5 h, or 0.1-0.3 h, or 0.1-0.2 h;

and/or, in step 1), the halogenated carboxylate is added dropwise, and optionally, the time of dropwise addition is 0-3 h, or 0-0.5 h.

6. The preparation method according to claim 2, wherein in step 1), the temperature of the condensation reaction is -20 °C to 80 °C or 15-60 °C or 15-40 °C or 20-30 °C;

and/or, in step 1), the time of the condensation reaction is 0.05-2 h, or 0.1-2 h, or 0.1-0.5 h, or 0.1-0.3 h, or 0.1-0.2 h;

and/or, in step 1), the halogenated carboxylate is added dropwise, and optionally, the time of dropwise addition is 0-3 h, or 0-0.5 h.

7. The preparation method according to claim 1, wherein in step 2), the acid-containing organic solvent has no water or has low water content;

and/or, in step 2), the acid-containing organic solvent comprises one or two of a methanol hydrogen chloride solution and an ethanol hydrogen chloride solution, and is optionally a methanol hydrogen chloride solution.

8. The preparation method according to claim 2, wherein in step 2), the acid-containing organic solvent has no water or has low water content;

and/or, in step 2), the acid-containing organic solvent comprises one or two of a methanol hydrogen chloride solution and an ethanol hydrogen chloride solution, and is optionally a methanol hydrogen chloride solution.

9. The preparation method according to claim 1, wherein in step 2), the method for purifying the precipitated halogenated inorganic salt to obtain a phenoxycarboxylate comprises: recycling the solvent and unreacted raw materials by means of distillation to obtain a phenoxycarboxylate; and optionally, the distillation method is negative-pressure distillation.

10. The preparation method according to claim 2, wherein in step 2), the method for purifying the precipitated halogenated inorganic salt to obtain a phenoxycarboxylate comprises: recycling the solvent and unreacted raw materials by means of distillation to obtain a phenoxycarboxylate; and optionally, the distillation method is negative-pressure distillation.

11. The preparation method according to claim 1, wherein in step 1), the method for preparing the salt of a phenolic compound comprises: allowing a phenolic compound and a metal hydroxide to subject to dehydration into salt in a polar solvent to obtain the salt of a phenolic compound; and optionally, the polar solvent is used as the polar solvent in step 1).

12. The preparation method according to claim 2, wherein in step 1), the method for preparing the salt of a phenolic compound comprises: allowing a phenolic compound and a metal hydroxide to subject to dehydration into salt in a polar solvent to obtain the salt of a phenolic compound; and optionally, the polar solvent is used as the polar solvent in step 1).

13. The preparation method according to claim 11, wherein the phenolic compound comprises one or more of phenol, o-cresol, 2,4-dichlorophenol and 4-chloro-2-methylphenol; and/or, the metal hydroxide comprises one or more of sodium hydroxide, potassium hydroxide, calcium hydroxide, magnesium hydroxide and aluminum hydroxide; optionally, the metal hydroxide comprises one or more of sodium hydroxide, potassium hydroxide and calcium hydroxide; optionally, the metal hydroxide is added in a form of an aqueous solution or a solid; and optionally, the mass fraction of the metal hydroxide is 30% or more.

14. The preparation method according to claim 11, wherein the condition for dehydration into salt is that dehydration into salt is performed with negative-pressure distillation; optionally, the intensity of pressure of negative-pressure distillation is −0.09 MPa to −0.098 MPa;

and/or, the mass ratio of the phenolic compound to the polar solvent is 1:1-20, or 1:2-18 in dehydration into salt;

and/or, the temperature of dehydration into salt is 50-120 °C, or 50-90 °C;

and/or, the time of dehydration into salt is 1-2 h.

15. The preparation method according to claim 13, wherein the condition for dehydration into salt is that dehydration into salt is performed with negative-pressure distillation; optionally, the intensity of pressure of negative-pressure distillation is −0.09 MPa to −0.098 MPa;

and/or, the mass ratio of the phenolic compound to the polar solvent is -1:1-20, or 1:2-18in dehydration into salt;

and/or, the temperature of dehydration into salt is 50-120 °C, or 50-90 °C;

and/or, the time of dehydration into salt is 1-2 h.

16. The preparation method according to claim 11, wherein the molar ratio of the phenolic compound to the metal hydroxide is 1:0.97-1, or 1:0.97-0.99, or 1:0.98 in dehydration into salt.

17. The preparation method according to claim 13, wherein the molar ratio of the phenolic compound to the metal hydroxide is 1:0.97-1, or 1:0.97-0.99, or 1:0.98 in dehydration into salt.

18. The preparation method according to claim 14, wherein the molar ratio of the phenolic compound to the metal hydroxide is 1:0.97-1, or 1:0.97-0.99, or 1:0.98 in dehydration into salt.

* * * * *